United States Patent
Wulfers

[11] 4,026,890
[45] May 31, 1977

[54] TRIAZINE-UREA GREASE THICKENERS

[75] Inventor: Thomas F. Wulfers, Hazelcrest, Ill.

[73] Assignee: Shell Oil Company, Houston, Tex.

[22] Filed: Nov. 26, 1975

[21] Appl. No.: 635,532

[52] U.S. Cl. .................. 260/249.6; 252/51.5 R
[51] Int. Cl.² .................................. C07D 251/70
[58] Field of Search ........................... 260/249.6

[56] References Cited
UNITED STATES PATENTS 3,309,345  3/1967  Lutwack ................. 260/249.6

Primary Examiner—John M. Ford

[57] ABSTRACT

Triazine-urea compounds having the structural formula

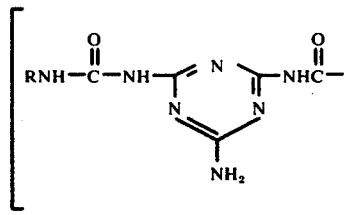

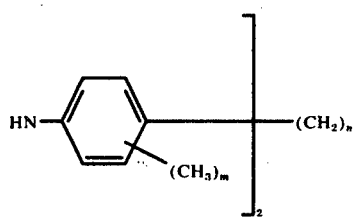

wherein R is an aliphatic hydrocarbyl radical of 16 to 22 carbon atoms, $m$ is 0 or 1 and $n$ is 0 or 1, are excellent thickening agents for greases employed in high temperature applications.

14 Claims, No Drawings

TRIAZINE-UREA GREASE THICKENERS

BACKGROUND OF THE INVENTION

This invention relates to a novel class of triazine-urea compounds useful as organic gellants for grease formulations. More particularly, this invention is directed to certain polyureido-s-triazine derivatives which are quite efficacious as high temperature grease thickening agents and to novel grease compositions gelled therewith.

In modern practice, it has become increasingly important that grease compositions be able to provide adequate lubrication at high temperature, e.g., temperatures of 350° F to 450° F or higher. Further, because many of the newer high temperature grease applications, e.g., high speed sealed bearings, require that the grease maintain a high level of lubricant activity for extended time periods, it is also essential that the thickener impart a high degree of mechanical stability on the grease formulation at such high temperatures.

A variety of thickening agents have been proposed for use in such high temperature applications including soap base thickeners, inorganic clay thickeners and organic thickening agents. Of these classes of thickening agents, the organic thickeners, specifically those containing urea or ureido functional groups, have been considered quite attractive because of their ashless nature and high temperature thickening properties. Examples of such organic thickening agents include polyureas and ureido compounds such as those described in U.S. Pat. Nos. 3,242,210, 3,243,372, 3,725,279 and 3,846,314, as well as dibenzimidazole-diureas disclosed in U.S. Pat. No. 3,752,765 and related arylcarbamyl thickeners described in U.S. Pat. No. 3,255,109. These organic thickeners are generally prepared by reacting one or more mono-, di- or polyamines with one or more mono-, di- or polyisocyanates, with the synthesis scheme in the case of the arylcarbamyl compounds involving the reaction of an aromatic amine with the reaction product of an aromatic diisocyanate and p-aminobenzoic acid.

While many of the aforementioned organic grease thickeners possess or retain their gellant properties in conventional mineral or synthetic hydrocarbon lubricant base oils at high temperatures, as shown by the high dropping points of greases formulated therefrom, they do not afford the extended operating lifetimes, as measured by thermal and mechanical stability at high temperatures, desired for sealed mechanical systems where lubricant life is a measure of mechanical life. Consequently, it would be quite desirable if an organic thickening agent could be developed in which high temperature gellant properties are combined with superior thermal and mechanical stability in such high temperature applications.

SUMMARY OF THE INVENTION

It has now been found that grease compositions having exceptional stability at high temperatures can be formulated by incorporating into the lubricating oil base vehicle, a triazine-urea compound of the formula:

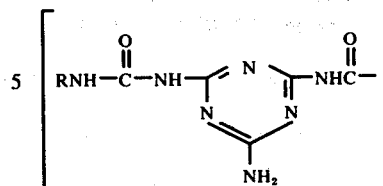

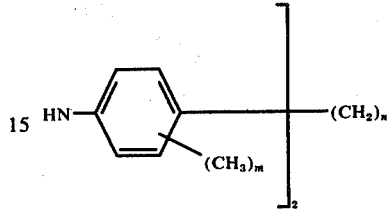

wherein R is an aliphatic hydrocarbyl radical of 16 to 22 carbon atoms and m and n are integers of 0–1, said triazine urea compound being incorporated in an amount sufficient to thicken the base vehicle to grease consistency. In addition to affording superior mechanical stability at high temperatures, the novel triazine-urea compounds of the invention show good thickening efficiency and produce greases with very high drop points, when formulated with conventional lubricating base oils.

Accordingly, the instant invention comprises the novel class of triazine-urea compounds described above and grease compositions thickened therewith.

DESCRIPTION OF THE PREFERRED EMBODIMENTS

As indicated above, the organic grease thickening agents of the invention are novel triazine-urea compounds of the formula:

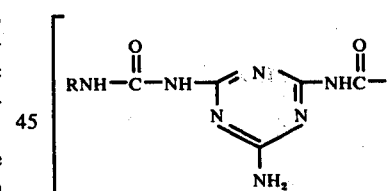

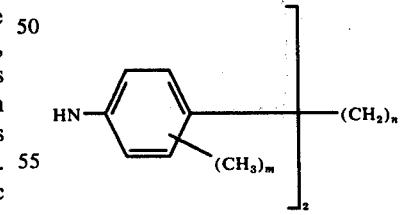

wherein R is an aliphatic hydrocarbyl radical of 16 to 22 carbon atoms and m and n are integers 0–1. By aliphatic hydrocarbyl is meant monovalent organic radicals made up of carbon and hydrogen. This substituent definition includes straight-chain or branched-chain, saturated or unsaturated aliphatic radicals. Preferably, the aliphatic hydrocarbyl substituent is a straight or branched-chain saturated aliphatic radical; most preferably, a straight-chain alkyl of 18 to 21 carbon atoms. In addition, from the standpoint of cost and availability of synthesis starting materials, it is preferred that m and n have values of 1 and 0, respectively.

Exemplary species of the compounds of the invention include:

4,4'-Bis[(6-octadecylureido,-4-amino-s-triazinyl-)ureido]-3,3'-dimethylbiphenyl
Bis[p-(6-octadecylureido-4-amino-s-triazinyl)ureido phenyl] methane
4,4'-Bis[(6-eicosylureido-4-amino-s-triazinyl-)ureido]-3,3'-dimethylbiphenyl The triazine-urea grease thickening agents of the invention are conveniently prepared via sequential reaction of an alkyl isocyanate (I) with melamine (triamino-s-triazine) (II) to produce a ureido-s-triazine intermediate (III), followed by reaction of the intermediate with a dinuclear aromatic diisocyanate (IV) in a 2:1 molar ratio of intermediate to diisocyanate to produce the desired triazine urea thickener (V). The procedure or reaction sequence is illustrated by the following equations employing the numeral designation for reactants and reaction products, given above:

EQUATION 1

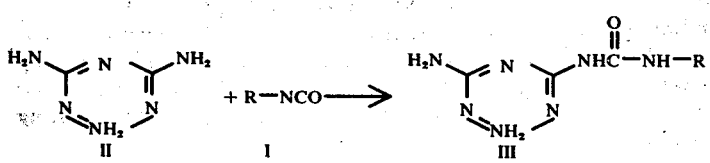

EQUATION 2

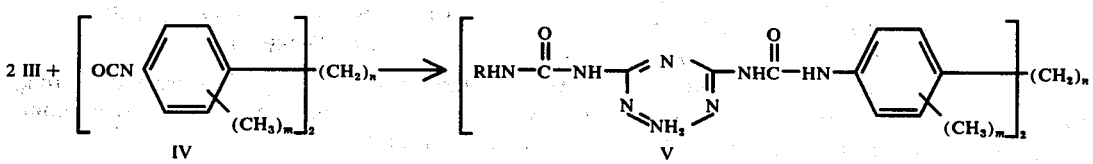

This reaction sequence can be carried out in situ by adding the reactants to the lubricating oil base vehicle in the sequence described, usually with the aid of a co-solvent, such as dimethyl formamide, which is subsequently stripped off. Preferably, the triazine-urea thickners of the invention are prepared in the absence of the base oil vehicle by sequential reaction in organic solvents selected on the basis of reactant solubility. In this preferred synthesis scheme the first reaction (equation 1) is suitably carried out in a polar organic solvent such as dimethyl formamide or dioxane while the final reaction step is advantageously carried out in an aromatic solvent such as xylene, toluene or benzene. Both reactions are suitably performed at elevated temperature, e.g., 100° to 200° C, with reaction time periods ranging from 15 minutes to 2 hours. When the triazine-urea thickener is prepared in the absence of the base lubricating oil, incorporation into the base oil is readily accomplished by converting the thickener to a fine powder with conventional grinding techniques, e.g., hammer mill, and adding the fine powder to the base oil with agitation at elevated temperatures, e.g., slow heating from ambient to 150° C. This warmed slurry of thickener in base oil can then be converted to a smooth grease by sequential milling and baking at elevated temperatures, e.g., 150° C.

Alkyl isocyanates which can be employed in preparing the triazine-urea grease thickeners of the invention include aliphatic monoisocyanates or mixtures of aliphatic monoisocyanates wherein the aliphatic substituent contains 16 to 22 carbon atoms. Suitable monoisocyanate reactants include straight-chain or branched-chain, saturated or unsaturated, aliphatic monoisocyanates. Preferably, the monoisocyanate reactant is a straight- or branched-chain, saturated aliphatic monoisocyanate having from 16 to 22 carbon atoms in the aliphatic substituent group (R group of the triazine-urea structural formula above). Most preferably, the monoisocyanate is a long-chain alkylisocyanate having a straight-chain alkyl group of 18 to 21 carbon atoms. Examples of such isocyanates include hexadecylisocyanate, heptadecenylisocyanate, nonadecylisocyanate, eicosylisocyanate, docosylisocyanate, 5-methylhexadecylisocyanate and hexadecenylisocyanate. Certain of the aliphatic monoisocyanate reactants employed in preparation of the triazine-ureas of the invention are available from commercial sources; others can be conveniently prepared from the corresponding amines by phosgenation of the amine hydrochloride.

The triazine reactant employed to prepare the organic grease thickeners of the invention is 2,4,6-triamino-S-triazine, otherwise commonly known as melamine. This triazine is conventionally prepared from starting materials such as urea and cyanuric acid or its chloride and is widely available commercially; being a basic starting material for a number of amino resins and plastics e.g., melamine-formaldehyde and melamine-urea-formaldehyde resins.

The dinuclear aromatic diisocyanates which may be employed as reactants in accordance with this invention include diphenylenediisocyanates and bis-[isocyanatophenyl]methanes optionally substituted on the aromatic rings with a methyl group. Specific examples of such isocyanates include diphenylmethane-4,4'-diisocyanate or bis-[p-isocyanato-phenyl]methane available as Multrathane M from Mobay Chemical Company, 3,3'-dimethylbiphenyl-4,4'-diisocyanate or bitolylene diisocyanate available as Isonate 136T from Upjohn Chemical Company, 3,3'-dimethyldiphenylmethane-4,4'-diisocyanate, and biphenyl-4,4'diisocyanate. Of these materials, bitolylene diisocyanate is particularly preferred as the diisocyanate reactant.

The thickening agents of the invention are generally employed in grease compositions in an amount sufficient to gel the lubricating oil or oleaginous base vehicle to grease consistency. This amount can vary, for example, from about 5–50% by weight of the total composition. Normally, however, with the good thickening efficiencies obtainable with the instant compounds, thickener concentrations of 10–35% by weight are sufficient to impart the desired consistency to base vehicle.

A wide variety of lubricating oils may be employed as the base vehicle in the present compositions. Suitable base oils include mineral lubricating oils such as naphthenic base, paraffin base or mixed base oils having a viscosity in the range of from 50 SSU at 100° F to 300 SSU at 210° F; synthetic hydrocarbon oils such as oligomerized alpha-olefins and oils derived from coal products; synthetic oils such as alkylene polymers, alkylene, oxide-type polymers; polyalkene glycols, polyethers, phosphate esters, dicarboxylic acid esters and pentaerythritol esters. The above oils may be used individually or in mixtures thereof, wherever miscible or made so by the use of solvents. Of the aforementioned base oils, mineral lubricating oils having viscosities of from about 400 to 700 SSU at 100° F are especially preferred.

In addition to the triazine-urea thickeners, the present compositions can also contain anticorrosion additives such as disodium sebacate, glyceryl monoleate, sodium sulfonates, sodium nitrite, amino- and benzotriazoles, and isostearamides or imidazolines of tetraethylenepentamine; oxidation inhibitors such as phenyl-alpha-naphthylamine, phenyl-beta-naphthlyamine, diphenylamines, phenothiazine, dithiocarbamates and various analogs and homologs thereof; viscosity index improvers such as methacrylate polymers and copolymers; extreme pressure agents, and any other additive recognized in the art to perform a particular function or functions.

The following illustrative embodiments depict the method of preparation of the present triazine-urea thickeners and their exceptional high temperature properties. It is to be understood, however, that these embodiments are presented for illustrative purposes only and that the invention in its broader aspects should not be limited thereto.

ILLUSTRATIVE EMBODIMENT I

A 200 ml round bottom flask equipped with magnetic stirring bar and a reflux condenser was charged with 12.6g of melamine in 120 ml of distilled dimethylformamide. The resulting solution was heated to incipient boiling and 29.5g of octadecylisocyanate (Mondur O Mobay Chemical Company) was added with stirring. The resulting mixture was brought to reflux and refluxed for about one hour under agitation. Heating was discontinued and the hot solution was filtered through a warm funnel. The filtrate was allowed to cool slowly, and the product which crystallized from the filtrate was separated by filtration. This product was washed with ether and dried in a vacuum oven. The yield was 40 grams of 2-octadecylureido-4-6-s-triazine having a melting point of 181°–185° C.

21g of the above product was charged to a 500 ml flask along with 300 ml of xylene. The flask was equipped with a magnetic stirring bar and a reflux condenser. 6.6 g of 4,4'-diisocyanato-3,3'-dimethylbiphenyl was added to the flask with stirring and the mixture was refluxed for about 12 hours; completion of the reaction being indicated by the disappearance of the isocyanate absorption band at 2240 cm$^{-1}$ in the infrared spectrum. Upon completion of the reflux period, the reaction mixture was cooled and the solvent removed on the rotary evaporator to yield a solid product. This solid product was ground to a powder in a mortar, stirred in 400 ml of ether, and then filtered. The filtered product was dried in a vacuum oven to yield 26g of 4,4'-bis[(6-octadecylureido-4-amino-s-triazinyl)ureido]-3,3'-dimethylbiphenyl.

ILLUSTRATIVE EMBODIMENT II

A thickened grease composition according to the invention was prepared from the triazine-urea product of Illustrative Embodiment I and an HVI 70/210 Neutral oil. To prepare this grease composition, 55.0g of the triazine-urea was ground to a fine powder with a mortar and pestle and stirred into 445.0g of the base oil while slowly heating to 150° C. This warmed slurry was milled on a three-roll paint mill (three passes being sufficient to produce a homogenous grease) and baked in an oven for about one hour at 150° C. The baked grease was cooled to about 90° C and milled again at 150° C through the three-roll paint mill to afford a smooth grease having an ASTM dropping point of 505° F and an ASTM worked penetration (D 217) (60 strokes) of 290.

ILLUSTRATIVE EMBODIMENT III

Utilizing the procedure of Illustrative Embodiment I, 40.5g of bis[p-(6-octadecylureido-4-amino-s-triazinyl)ureido)phenyl] methane was synthesized from melamine (9.9g), octadecylisocyanate (20.0g) and 4,4'-diisocyanatodiphenylmethane (10.8g). This triazine-urea thickener (30.0g) was formulated with HVI 70/210 Neutral Oil (170.0g) according to the procedure described in Illustrative Embodiment II to yield a smooth grease having an ASTM dropping point of 520° F and a modified (1/4 scale) worked penetration (60 strokes) of 69. This penetration was determined using a modification of the grease workers' test ASTM D 217A wherein a cylindrical plug was inserted in the grease worker cup to reduce the volume of grease necessary for the test from approximately 300 to 75 ml and the penetration measured with a one-quarter scale penetrameter.

ILLUSTRATIVE EMBODIMENT IV

A series of grease compositions containing various triazine-urea thickening agents according to the invention were prepared using the procedure described in Illustrative Embodiments I and II. These greases, fully formulated with commercial additives, were tested in a variety of conventional grease tests to demonstrate their mechanical stability at high temperatures. The test results, as well as descriptions of the thickeners and grease formulations employed and other standard properties of the thickened grease compositions, are presented in Table I.

Table I

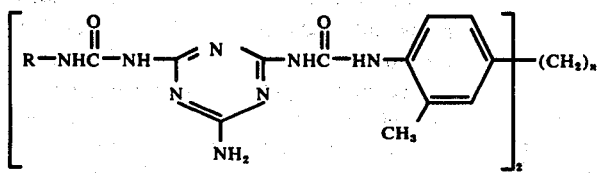

| Thickener Composition | Thickener Structural Formula | | | |
|---|---|---|---|---|
| | R=$C_{18}H_{37}$ n=0 | R=$C_{19}H_{39}$ (ave) n=0 | R=$C_{20}H_{41}$ (ave) n=0 | R=$C_{21}H_{43}$ (ave) n=0 |
| ASTM Penetration at 0 and 60 strokes | | | | |
| Thickener 15% | 227/253 | 155/174 | 167/189 | 170/193 |
| 11% | 279/298 | 204/212 | 219/242 | 249/275 |
| Efficiency, % Thickener | 11 | 9.5 | 9.5 | 10.5 |
| Drop Point, °F[a] | 505 | 515 | 505 | 495 |
| Worked Stability[b] Penetration at 0 strokes | 252 | 268 | | 249 |
| Penetration at 60 strokes | 272 | 294 | | 275 |
| Penetration at 1,000 strokes | 287 | 320 | | 294 |
| Penetration at 10,000 strokes | 305 | 342 | | 332 |
| Penetration at 100,000 strokes | 316 | 362 | | 350 |
| Change from 60 to 100,000 strokes | +44 | +68 | | +75 |
| Roll Test at Room[c] Temperature, Hrs. | 500 | 500 | | |
| ¼ Scale Penetration[d] at 500 hrs. | 83 | 93 | | |
| Cone Bleed at 360° F,%[e] | 12 | 12 | | |
| 350° F Pope Bearing Rig[f] Life, Hrs. | | | | |
| Formulation A[g] | 307[D] | 464[D] | | 430[D] |
| Formulation B[h] | 560[D] | 620[D] | | 635[D] |
| 312° F Navy Bearing Rig[j] Life, Hrs. | | | | |
| Formulation A[g] | 3500, 2096 | | | |
| 325° F Rig Life, Hrs. | | | | |
| Rig A (Alternator Rig)[k] | | | | |
| Formulation A[g] | 115, 37 | | | |
| Formulation B[h] | 195, 176 | | | |
| Rig B[l] | | | | |
| Formulation A[g] | 891, 941 | | | |
| Formulation B[h] | 706, 336, 448 | | | |

[a]ASTM Test Method D-566 (base oil + thickener, only).
[b]base oil + thickener only (all penetrations measured on ¼ scale and converted to full scale via correlation chart.
[c]ASTM D-1831
[d]determined according to method of Illustrative Embodiment III
[e]FTMS 791a Method 321
[f]Federal Test Method Standard 791a, Method 333-204S-17 Bearing, 10 M rpm, 15 lb radial load, cyclic operation.
[g]fully formulated - 1% Irganox LO-6, 1% Irganox LO-4, 1% sodium sebacate.
[h]fully formulated - 1.5% Vanlube 81, 1% Irganox LO-6, 1% sodium sebacate.
[D]average of at least two runs.
[j]Federal Test Methods 331.1 - 204 K Bearking, 10 M rpm, 10 lb axial load, 3 lb radial load, continuous running.
[k]Test conditions, 250 lb radial load, 203 bearing, 10 M rpm, continuous running.
[l]Test conditions, 204 K Bearing, 10 M rpm, 100 lb radial load, continuous running.

Note: Base Oil employed in all formulations was a mineral lubricating oil having a viscosity of 580 SSU at 100° F. Thickener where R=$C_{18}H_{37}$ derived from octadecyl isocyanate. Thickener where R=$C_{19}H_{39}$ ave. derived from mixture of alkyl isocyanates having an average alkyl chain length of 19 carbon atoms which, in turn, were prepared via phosgenation of kemamine 1500 (Humko Chemical Co.) consisting of 20% $C_{16}$, 30% $C_{18}$, 25% $C_{20}$ and 25% $C_{22}$ amines. Thickener where R=$C_{20}H_{41}$ ave. derived from mixture of alkyl isocyanates having an average alkyl chain length of 20 carbon atoms which, in turn, were prepared via phosgenation of Adogen 101D (Ashland Chemical Co.) consisting of 10% $C_{16}$, 20% $C_{18}$, 30% $C_{20}$ and 40% $C_{22}$ amines. Thickener where R=$C_{21}H_{43}$ derived from mixture of alkyl isocyanates having an average alkyl chain length of 21 carbon atoms which, in turn, were prepared via phosgenation of kemamine 190D (Humko Chemical Co.) consisting of 10% $C_{18}$, 45% $C_{20}$ and 45% $C_{22}$ amines.

What is claimed is:

1. A triazine-urea compound defined by the formula:

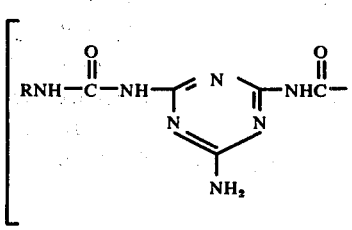

-continued

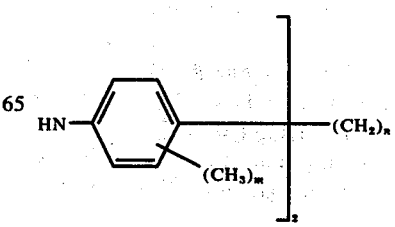

wherein R is an aliphatic hydrocarbyl radical of 16 to 22 carbon atoms and $m$ and $n$ are integers of 0–1.

2. A compound according to claim 1, wherein R is selected from the class consisting of straight-chain and branched-chain saturated aliphatic hydrocarbyl radicals of 16 to 22 carbon atoms and straight-chain and branched-chain unsaturated aliphatic hydrocarbyl radicals of 16 to 22 carbon atoms.

3. A compound according to claim 2, wherein R is a straight-chain alkyl of 18 to 21 carbon atoms.

4. A compound according to claim 3, wherein $m$ is 1 and $n$ is 0.

5. The compound of claim 2 wherein R is selected from the class consisting of straight-chain and branched-chain saturated aliphatic hydrocarbyl radicals of 16 to 22 carbon atoms.

6. The compound of claim 5 wherein R is $C_{18}H_{37}$—.
7. The compound of claim 5 wherein R is $C_{19}H_{39}$—.
8. The compound of claim 5 wherein R is $C_{20}H_{41}$—.
9. The compound of claim 5 wherein R is $C_{21}H_{43}$—.
10. 4,4'-Bis[(6-octadecylureido,-4-amino-S-triazinyl)ureido]-3,3'-dimethylbiphenyl.
11. Bis[p-(6-octadecylureido-4-amino-S-triazinyl)ureido phenyl] methane.
12. 4,4'-Bis[(6-eicosylureido-4-amino-S-triazinyl)ureido]-3,3'-dimethylbiphenyl.
13. 4,4'-Bis[(6-nonadecylureido-4-amino-S-triazinyl)ureido]-3,3'-dimethylbiphenyl.
14. 4,4'-Bis[(6-heneicosylureido-4-amino-S-triazinyl)ureido]-3,3'-dimethylbiphenyl.

* * * * *